(12) United States Patent
Deng et al.

(10) Patent No.: US 10,647,962 B2
(45) Date of Patent: *May 12, 2020

(54) BIOACTIVE ALUMINOBORATE GLASSES (71) Applicant: Corning Incorporated, Corning, NY (US)

(72) Inventors: Huayun Deng, Painted Post, NY (US); Ye Fang, Painted Post, NY (US); Qiang Fu, Painted Post, NY (US); John Christopher Mauro, Corning, NY (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/602,819

(22) Filed: May 23, 2017

(65) Prior Publication Data
US 2017/0342382 A1 Nov. 30, 2017

Related U.S. Application Data (60) Provisional application No. 62/342,384, filed on May 27, 2016.

(51) Int. Cl.
| C12N 5/077 | (2010.01) |
| C03C 3/19 | (2006.01) |
| C03C 4/00 | (2006.01) |
| A61L 27/54 | (2006.01) |
| A61L 27/10 | (2006.01) |
| A61K 35/32 | (2015.01) |

(52) U.S. Cl.
CPC ............ *C12N 5/0654* (2013.01); *A61K 35/32* (2013.01); *A61L 27/105* (2013.01); *A61L 27/54* (2013.01); *C03C 3/19* (2013.01); *C03C 4/0014* (2013.01); *C03C 4/0035* (2013.01); *A61L 2300/102* (2013.01); *C03C 2204/00* (2013.01); *C12N 2501/105* (2013.01); *C12N 2501/11* (2013.01); *C12N 2501/115* (2013.01); *C12N 2501/165* (2013.01); *C12N 2533/12* (2013.01)

(58) Field of Classification Search
CPC . A61K 35/32; A61L 2300/102; A61L 27/105; A61L 27/54; C03C 3/19; C03C 4/0014; C03C 4/0035; C12N 2501/105; C12N 2501/11; C12N 2501/115; C12N 2501/165; C12N 2533/12; C12N 5/0654
See application file for complete search history.

(56) References Cited

U.S. PATENT DOCUMENTS

| 2,532,386 | A | 12/1950 | Armistead |
| 2,978,339 | A | 4/1961 | Veatch et al. |
| 3,323,888 | A | 6/1967 | Searight et al. |
| 3,778,335 | A | 12/1973 | Boyd |
| 3,790,430 | A | 2/1974 | Mochel |
| 4,083,727 | A | 4/1978 | Andrus et al. |
| 4,084,972 | A | 4/1978 | Andrus et al. |
| 4,126,437 | A | 11/1978 | O Horo |
| 4,140,645 | A | 2/1979 | Beall et al. |
| 4,233,169 | A | 11/1980 | Beall et al. |
| 4,323,056 | A | 4/1982 | Borrelli et al. |
| 4,340,693 | A | 7/1982 | Drake |
| 4,889,707 | A | 12/1989 | Day |
| 5,081,394 | A | 1/1992 | Morishita et al. |
| 5,153,070 | A | 10/1992 | Andrus |
| 5,648,124 | A | 7/1997 | Sutor |
| 5,674,790 | A | 10/1997 | Araujo |
| 5,849,816 | A | 12/1998 | Suskind et al. |
| 5,876,452 | A | 3/1999 | Athanasiou et al. |
| 6,214,471 | B1 | 4/2001 | Beall |
| 6,254,981 | B1 | 7/2001 | Castle |
| 6,280,863 | B1 | 8/2001 | Frank et al. |
| 6,328,990 | B1 | 12/2001 | Ducheyne et al. |
| 6,338,751 | B1 | 1/2002 | Litkowski et al. |
| 6,506,399 | B2 | 1/2003 | Donovan |
| 6,514,892 | B1 | 2/2003 | Kasai et al. |
| 6,802,894 | B2 | 10/2004 | Brodkin |
| 6,852,656 | B1 | 2/2005 | La Greca et al. |
| 6,838,171 | B2 | 6/2005 | Nomura |

(Continued)

FOREIGN PATENT DOCUMENTS

| CA | 2577628 C | 11/2010 |
| CA | 2926665 A1 | 5/2015 |

(Continued)

OTHER PUBLICATIONS

Ohgushi et al. Bioceramics vol. 11, LeGeros et al, Ed., Proc. 11th Int. Symp. Ceramics Med. (NY: NY), Nov. 1998, pp. 261-264 (Year: 1998).*
Andersson et al. J. Mat. Science: Materials in Medicine (1990) 1: 219-227 (Year: 1990).*
L. Hench et al., "Third-Generation Biomedical Materials", Science, vol. 295, Feb. 8, 2002, p. 1016-1017, www.sciencemag.org, Downloaded from www.sciencemag.org on Aug. 5, 2015.
L.L.Hench, "Bioceramics", J. Am. Ceram. Soc., 81, (7), 1705-1728 (1998).
T. Kokubo et al., "How useful is SBF in predicting in vivo bone bioactivity?", Biomaterials, 27, (2006), 2907-2915.
Qiang Fu et al., "Bioactive glass scaffolds for bone tissue engineering: state of the art and future perspectives", Materials Science and Engineering, C 31, (2011), 1245-1256.

(Continued)

*Primary Examiner* — Susan M Hanley (57) ABSTRACT

An aluminoborate glass composition, including $B_2O_3$, $Al_2O_3$, $P_2O_5$, $Na_2O$, and $CaO$, as defined herein. Also disclosed are bioactive compositions including the disclosed aluminoborate glass composition, a suitable fluid, and at least one live cell. Also disclosed is method of limiting the amount of boron released into an aqueous solution from a disclosed aluminoborate-containing glass composition as defined herein. Also disclosed is a method of proliferating cells on a bioactive substrate as defined herein.

16 Claims, 7 Drawing Sheets

(56) References Cited

U.S. PATENT DOCUMENTS

| | | |
|---|---|---|
| 7,166,548 B2 | 1/2007 | Apel et al. |
| 7,166,549 B2 | 1/2007 | Fechner et al. |
| 7,597,900 B2 | 10/2009 | Zimmer et al. |
| 7,704,903 B2 | 4/2010 | Seneschal et al. |
| 7,709,027 B2 | 5/2010 | Fechner et al. |
| 7,905,115 B2 | 3/2011 | Rake et al. |
| 7,989,065 B2 | 8/2011 | Winstead |
| 8,080,490 B2 | 12/2011 | Fechner et al. |
| 8,173,154 B2 | 5/2012 | Jung et al. |
| 8,637,300 B2 | 1/2014 | Ruf et al. |
| 9,056,045 B2 | 6/2015 | Hughes |
| 9,084,844 B2 | 7/2015 | Vallittu |
| 9,168,272 B2 | 10/2015 | Hill et al. |
| 9,241,879 B2 | 1/2016 | Castillo |
| 9,326,995 B2 | 5/2016 | Stucky et al. |
| 9,498,459 B2 | 11/2016 | Pomrink et al. |
| 9,622,483 B2 | 4/2017 | Bookbinder et al. |
| 9,688,567 B2 | 6/2017 | Rampf et al. |
| 9,701,573 B2 | 7/2017 | Beall et al. |
| 2004/0120908 A1 | 6/2004 | Cohen et al. |
| 2004/0228905 A1 | 11/2004 | Greenspan et al. |
| 2005/0118236 A1 | 6/2005 | Qiu et al. |
| 2005/0142077 A1 | 6/2005 | Zimmer et al. |
| 2005/0158395 A1 | 7/2005 | Zimmermann et al. |
| 2006/0127427 A1 | 6/2006 | Vernice et al. |
| 2006/0292280 A1 | 12/2006 | Soper et al. |
| 2007/0122356 A1 | 5/2007 | Kessler et al. |
| 2008/0214428 A1 | 9/2008 | Orlich et al. |
| 2008/0233201 A1 | 9/2008 | Royere |
| 2009/0208428 A1 | 8/2009 | Hill |
| 2011/0009254 A1 | 1/2011 | Schweiger et al. |
| 2011/0152057 A1 | 6/2011 | Qi |
| 2012/0020898 A1 | 1/2012 | Mandadi et al. |
| 2012/0135848 A1 | 5/2012 | Beall et al. |
| 2012/0317735 A1 | 12/2012 | Gonzales |
| 2012/0321567 A1 | 12/2012 | Gonzales |
| 2013/0266625 A1 | 10/2013 | Benita |
| 2014/0026916 A1 | 1/2014 | Havens |
| 2014/0186274 A1 | 7/2014 | Hodgkinson |
| 2014/0193499 A1 | 7/2014 | Da Fonte Ferreira |
| 2014/0212469 A1 | 7/2014 | Rahaman |
| 2014/0219941 A1 | 8/2014 | Takekawa et al. |
| 2014/0271913 A1 | 9/2014 | Pomrink et al. |
| 2014/0349831 A1* | 11/2014 | Cornejo .................. C03C 3/064 501/52 |
| 2014/0370464 A1 | 12/2014 | Kounga et al. |
| 2015/0087493 A1 | 3/2015 | Ritzberger |
| 2015/0104655 A1 | 4/2015 | Kim et al. |
| 2015/0231042 A1 | 8/2015 | Gonzales |
| 2015/0239772 A1 | 8/2015 | Baker |
| 2015/0265509 A1 | 9/2015 | Zhang et al. |
| 2015/0299031 A1 | 10/2015 | Ritzberger et al. |
| 2015/0374589 A1 | 12/2015 | Rampf et al. |
| 2016/0102010 A1 | 4/2016 | Beall et al. |
| 2016/0145567 A1 | 5/2016 | Henry et al. |
| 2016/0340239 A1 | 11/2016 | Propster et al. |
| 2017/0086877 A1 | 3/2017 | Moffarah et al. |
| 2017/0274118 A1 | 9/2017 | Nazhat et al. |
| 2017/0340527 A1 | 11/2017 | Chang et al. |
| 2017/0340666 A1 | 11/2017 | Deng et al. |
| 2017/0341975 A1 | 11/2017 | Gross et al. |
| 2017/0342383 A1 | 11/2017 | Deng et al. |
| 2017/0349876 A1 | 12/2017 | Deng et al. |
| 2017/0354755 A1 | 12/2017 | Weinberger et al. |
| 2018/0343255 A1 | 11/2018 | Thibadeau, Sr. et al. |

FOREIGN PATENT DOCUMENTS

| | | |
|---|---|---|
| EP | 583791 A1 | 2/1994 |
| EP | 935526 A1 | 8/1999 |
| EP | 1452496 A1 | 9/2004 |
| EP | 1021148 B1 | 5/2008 |
| HU | 227595 B1 | 9/2011 |
| JP | 2004359754 A | 12/2004 |
| JP | 2007001846 A | 1/2007 |
| JP | 2007039269 A | 2/2007 |
| KR | 200781952 | 8/2007 |
| KR | 2013112433 A | 10/2013 |
| WO | 1991021032 A1 | 8/1991 |
| WO | 1997018171 A1 | 5/1997 |
| WO | 199727148 A1 | 7/1997 |
| WO | 9962835 A1 | 12/1999 |
| WO | 2007141978 A1 | 12/2007 |
| WO | 2008000888 A2 | 1/2008 |
| WO | 2011141896 A1 | 11/2011 |
| WO | 2012137158 | 10/2012 |
| WO | 2014095198 A1 | 6/2014 |
| WO | 2014159240 A1 | 10/2014 |
| WO | 2015034860 | 3/2015 |
| WO | 2015123049 A1 | 8/2015 |
| WO | 2015200017 A1 | 12/2015 |

OTHER PUBLICATIONS

L. Peddi et al., "Bioactive borate glass coatings for titanium alloys", J. Mater. Sci: Mater. Med., (2008), 19, p. 3145-3152.

Mohamed N. Rahaman et al., "Bioactive glass in tissue engineering", Acta Biomaterialia, 7, (2011), 2355-2373.

WO2012137158 machine translation, published Oct. 11, 2012.

Dutra Zanotto, "A bright future for glass-ceramics", American Ceramic Society Bulletin, vol. 89, No. 8, pp. 19-27, 2010.

American Type Culture Collection, Product Sheet MC3T3E1, Subclone 14, (ATCC® CRL2594™), p. 1-3, Aug. 2014.

Maziar Montazerian, et al. "History and trends of bioactive glass-ceramics", Journal of Biomedical Materials Research A, 2016, vol. 104A, 1231-1249, 2016 Wiley Periodicals, Inc.

Apel et al., "Influence of ZrO2 on the crystallization and properties of lithium disilicate glass-ceramics derived from a multi-component system", J Eur Ceram Soc, 2007, 27:1571-1577.

Antonio Tilocca et al., "Structural Effects of Phosphorus Inclusion in Bioactive Silicate Glasses", J. Phys. Chem. B 2007, 111, 14256-14264.

K. Franks et al., "The effect of MgO on the solubility behaviour and cell proliferation in a quaternary soluble phosphate baed glass system", J. of Mate. Sciemce: Materials in Medicine, 13, (2002), 549-556.

I. Ahmed et al., "Processing, characterisation and biocompatibility of iron-phosphate glass fibres for tissue engineering", Biomaterials, 25, (2004), 3223-3232.

Huipin Yuan, et al., "Osteoinduction by calciumphosphate biomaterials", Journal of Materials Science: Materials in Medicine 9 (1998) 723-726.

Jianxi Lu, et al,, The Biodegradation Mechanism of Calcium Phosphate Biomaterials in Bone, Journal of Biomedical Materials Research, Aug. 2002, 63(4): 408-412.

B.C. Bunker, et al., Phosphate Glass Dissolution in Aqueous Solutions, Journal of Non-Crystalline Solids 64 (1984) 291-316.

Jonathan C. Knowles, Phosphate based glasses for biomedical applications, J. Mater. Chem., 2003, 13, 2395-2401.

Motohiro Uo et al., Properties and cytotoxicity of water soluble Na2O—CaO—P2O5 glasses, Biomaterials, 19, (1998), 2277-2284.

F. Jay Murray, Issues in Boron Risk Assessment: Pivotal Study, Uncertainty Factors, and ADIs, The Journal of Trace Elements in Experimental Medicine 9, No. 4 (1996): 231-243.

R.F. Brown, et al., "Effect of borate glass composition on its conversion to hydroxyapatite and on the proliferation of MC3T3-E1 cells." Journal of Biomedical Materials Research Part A, 88, No. 2, (2009): 392-400.

A. Saranti, et al., "Bioactive glasses in the system CaO—B2O3—P2O5: preparation, structural study and in vitro evaluation." Journal of Non-Crystalline Solids 352, No. 5 (2006): 390-398.

L. Hench, and J. Jones, eds. Biomaterials, artificial organs and tissue engineering. Elsevier, 2005—book.

E.A. Abou Neel,et al., "Effect of iron on the surface, degradation and ion release properties of phosphate-based glass fibres." Acta Biomaterialia 1, No. 5 (2005): 553-563.

(56) References Cited

OTHER PUBLICATIONS

E.A. Abou Neel, et al., "Characterisation of antibacterial copper releasing degradable phosphate glass fibres.", Biomaterials 26, No. 15 (2005): 2247-2254.
C. M. Rochman, et al., Scientific evidence supports a ban on microbeads, Environ Sci & Tech, 2015, 49: 10759-10761.
Wei Xiao et al., "Hollow hydroxyapatite microspheres: a novel bioactive and osteoconductive carrier for controlled release of bone morphogenetic protein-2 in bone regeneration", Acta Biomater. Sep. 2013 ; 9(9): 8374-8383.
Wanpeng Cao et al., Bioactive Materials, Ceramics International, 22, (1996) 493-507.
Fabienne C. Raszewski et al., Methods for Producing Hollow Glass Microspheres, Savannah River National Laboratory, Aiken, SC 29808, Mar. 2016.
Imogen E. Napper et al., Characterisation, quantity and sorptive properties of microplastics extracted from cosmetics, Marine Pollution Bulletin, vol. 99, Issues 1-2, Oct. 15, 2015, pp. 178-185.
Alexis J. de Kerchove et al., Formation of Polysaccharide Gel Layers in the Presence of Ca2+ and K+ Ions: Measurements and Mechanisms, Biomacromolecules, 2007, 8, 113-121.
Marianne Hiorth et al., Immersion coating of pellets with calcium pectinate and chitosan, International Journal of Pharmaceutics 308 (2006) 25-32.
Fuat Topuz, et al., Magnesium ions and alginate do form hydrogels: a rheological study, Soft Matter, 2012, 8, 4877-4881.
Yrr A. Mørch, et al., Effect of Ca2+, Ba2+, and Sr2+ on Alginate Microbeads, Biomacromolecules 2006, 7, 1471-1480.
International Search Report and Written Opinion PCT/US2017/034384 dated Aug. 7, 2017.
Bertling, et al., "Hollow microspheres". Chem Eng Technol, 2004, 27: 829-837.
Fu, H., et al., "Hollow hydroxyapatite microspheres as a device for controlled delivery of proteins". J Mater Sci: Mater Med., 2011, 22: 579-591.
Huang, et al., "Kinetics and mechanisms of the conversion of silicate (45S5), borate and borosilicate glasses to hydroxyapatite in dilute phosphate solutions," J Mater Sci Mater Med 2006, 17: 583-596.
V. V. Budov, "Hollow glass microspheres. Use, properties and technology (review article)", Glass Ceram, 1994, 51: 230-235.
Pires et al; "The Role of Alumina in Aluminoborosilicate Glasses for Use in Glass-Ionomer Cements"; J. Mater. Chem, 19 (2009) pp. 3652-3660.
Abo-Naf et al; "In Vitro Bioactivity Evaluation, Mechanical Properties and Microstructural Characterization of Na2O—CaO—B2O3—P2O5 Glasses"; Spectrochimica Acta Part A: Molecular and Biomolecular Spectroscopy; 144 (2015) pp. 88-98.
Buchilin et al; "Crystallization-Controlled Pore Retention in Calcium-Phosphate Glassceramics From Powder Sintering of CaO—P2O5—B2O3—Al2O3—TiO2—ZrO2 Glass"; Journal of Non-Crystalline Solids; 373-374 (2013) pp. 42-50.
Cao et la; "Methods for Biomimetic Remineralization of Human Dentine: A Systematic Review"; Int. J. Mol. Sci. (2015) 16; pp. 4615-4627.
Copeland et al; "Microbeads: An Emerging Water Quality Issue", Retrieved From fas.org, Jul. 20, 2015, 2 Pgs.
Coradin et al; "Silica-Alginate Composites for Microencapsulation" Applied Microbiology and Biotechnology, 61(5-6) pp. 429-434 (2003.
Davari, "Dentin Hypersensitivity: Etiology, Diagnosis and Treatment, A Literature Review," J Dent (Shiraz), 2013, 14(3): 136145).
Noris-Suarez et al; "Osteoblastic Cells Biomineralized on Bioactive Glass and Glass-Ceramics of the SiO2Na20.CaO.K2O.MgO.P2O5 System Modified With Al2O3 and B2O3"; Journal of Ceramic Processing Research; vol. 11, No. 2 (2010) pp. 129-137.
El-Kheshen et al. Ceramics Int. (2008) 34: 1667-1673 (Year: 2008).
Fendall et al; "Contributing to Marine Pollution by Washing Your Face: Microplasitcs in Facial Cleansers"; Marine Pollution Bulletin 58 (8): 12251228 (2009.

Forsback et al; "Mineralization of Dentin Induced by Treatment With Bioactive Glass S53P4 In Vitro"; Acta Odontol Scand, 62 (2004); pp. 14-20.
Fu et al; "Bioactive Glass Innovations Through Academia-Industry Collaboration"; International Journal of Applied Glass Science, 7 [2], (2016) pp. 139-146.
Fu et al; "Nature-Inspired Design of Strong, Tough Glass-Ceramics," MRS Bulletin, 2017, 42:220-225.
Graham, "High-Sensitivity Manetization Measurements", J. Mater. Sci. Technol., vol. 16, No. 2, 2000, p. 97-101.
Gy, "Ion Exchange for Glass Strengthening," Mater Sci EHG B, 2008, 149: 159-165.
Han et al; "In Vivo Remineralization of Dentin Using an Agarose Hydrogel Biomimetic Mineralization System"; Nature, Scientific Reports; (2017); 9 Pages.
Holand et al; "A Comparison of the Microstructure and Properties of the IPS EMPRESST2 and the IPS EMPRESST Glass-Ceramics"; J Biomed Mater Res (Appl Biomater), 2000, 53: 297303.
Jacoby; "New Applications for Glass Emerge," Chem. Eng. News, 90 [25] 3436 (2012).
Jones; "Review of Bioactive Glass: From Hench to Hybrids"; ACTA Biomaterialia 9 (2013) pp. 4457-4486.
Kulal et al; "An In-Vitro Comparison of Nano Hydroxyapatite, Novamin and Proargin Desensitizing Toothpastes—A SEM Study"; Journal of Clinical and Diagnostic Research; 2016; vol. 10 (10) ZC51-ZC54.
Kumaryadav et al; "Development of Zirconia Substituted 1393 Bioactive Glass for Orthopaedic Application"; Oriental Journal of Chemistry; vol. 33, No. 6; (2017) pp. 2720-2730.
Lien et al; "Microstructural Evolution and Physical Behavior of a Lithium Disilicate Glass-Ceramic"; Dent Mater 2015, 31: 928-940.
Low et al; "Reduction in Dental Hypersensitivity With Nano-Hydroxyapatite, Potassium Nitrate, Sodium Monoflurophosphate and Antioxidants"; The Open Dentistry Journal; (2015), 9, pp. 92-97.
Marcolongo et al; "Surface Reaction Layer Formation In Vitro on a Bioactive Glass Fiber/Polymeric Composite"; J. Biomed Mater. Res.; (1997); 37, pp. 440-448.
Miglani et al; "Dentin Hypersensitivity: Recent Trends in Management"; J. Conserv. Dent. 2010; 13 (4) pp. 218-224.
Mintatoya et al; "Bioactive Glass Cloth That Propmotes New Bone Formation"; Key Eng. Mater.; (2013) 529-530; pp. 266-269.
Ramanujan, Book Chapter 17, Magnetic Particles for Biomedical Applications, R. Narayan (ed.), Biomedical Materials, DOI 10.1007/978-0-387-84872-3 17, C Springer Science+Business Media, LLC 2009, pp. 477-491.
Sglavo; "Chemical Strengthening of Soda Lime Silicate Float Glass: Effect of Small Differences in the KNO3 Bath," Int J Appl Glass Sci, 2015, 6: 72-82.
Sharmin et al; "Effect of Boron Additiona on the Thermal, Degradation, and Cytocompatibility Properties of Phosphate-Based Glasses"; Biomed Research Internaitonal; vol. 2013; Article ID 902427; 12 Pages.
Simhan; "Chemical Durability of ZrO2 Containing Glasses"; Journal of Non-Crystalline Solids; 54 (1983) 335-343.
Singh et al; "Characterization of Si02—Na20—Fe203—Ca0—P205_B203 Glass Ceramics"; Journal of Materials Science: Materials in Medicine, 10(8) pp. 481-484. (1999.
Succaria et al; "Prescribing a Dental Ceramic Material: Zirconia vs Lithium-Disilicate"; The Saudi Dent J, 2011, 23: 165-166.
Wallenberger et al; "The Liquidus Temperature; Its Critical Role in Glass Manufacturing"; International Journal of Applied Glass Science 1 [2] (2010) pp. 151-163.
Yao et al; "In Virto Bioactive Characteristics of Borate-Based Glasses With Controllable Degradation Behavior"; J. Am. Ceram. Soc.; 90 [1]; 303-306 (2007.
Yin et al; "Effect of ZrO2 on the Bioactivity Properties of Gel-Derived CaO—P2O5—SiO2—SrO Glasses"; Ceramics International; 43 (2017) pp. 9691-9698.
Yue et al; "Fiber Spinnability of Glass Melts"; International Journal of Applied Glass Science; (2016) pp. 1-11.
Zhang et al; "Chipping Resistance of Graded Zirconia Ceramics for Dental Crowns"; J Dent Res, 2012, 91:311315.

(56) References Cited

OTHER PUBLICATIONS

Zheng et al; "Characteristics and Biocompatibility of Na2O—K2O—CaO—MgO—SrO—B2O3—P2O5 Borophosphate Glass Fibers"; Journal of Non-Crystalline Solids; 358 (2012) 387-391.
Mohini et al; "Studies on Influence of Aluminium Ions on the Bioactivity of B2O3—SiO2—P2O5—Na2O—CaO Glass System by Means of Spectroscopic Studies"; Applied Surface Science; 287 (2013) pp. 46-53.
Gorustovich et al. "Osteoconductivity of strontium-doped bioactive glass particles: A histomorphometric study in rats," J Biomed Materials Res. Part A (2010) 92A: pp. 232-237.
Kaklamani et al: "Mechanical Properties of Alginate Hydrogels Manufactured Using External Gelation", J. Meech Beh. Biomed, Mater., 2014, pp. 135-142 (Year: 2014).
Harianawala et al. "Biocompatibility of Zirconia", J Adv Med Deni Sci Res 4(3) 2016, pp. 35-39.
Strassler et al; "Dentinal Hypersensitivity: Etiology, Diagnosis and Management"; 9 Pages; Date Unknown; www.indeedce.com.
"Azo Materials, ""Silicon Dioxide""", accessed from: ""https://www.azom.com/properties.aspx?ArticleI D=1114"", accessed on Feb. 19, 2019,pp. 1-4 (Year: 2019)".

\* cited by examiner

BIOACTIVE ALUMINOBORATE GLASSES

This application claims the benefit of priority under 35 U.S.C. § 119 of U.S. Provisional Application Ser. No. 62/342,384 filed on May 27, 2016 the content of which is relied upon and incorporated herein by reference in its entirety.

CROSS-REFERENCE TO RELATED APPLICATIONS

The present application is related commonly owned and assigned USSN Provisional Applications Serial Nos., filed concurrently herewith:

62/342,377, entitled "MAGNETIZABLE GLASS CERAMIC COMPOSITION AND METHODS THEREOF";

62/342,381, entitled "LITHIUM DISILICATE GLASS-CERAMIC COMPOSITIONS AND METHODS THEREOF";

62/342,391, entitled "BIODEGRADABLE MICRO-BEADS";

62/342,411, entitled "BIOACTIVE GLASS MICRO-SPHERES"; and

62/342,426, entitled "BIOACTIVE BOROPHOSPHATE GLASSES", but does not claim priority thereto.

The present application is also related to commonly owned and assigned USSN Provisional Application Ser. No. 62/189,880 filed Jul. 7, 2015, entitled "ANTIMICROBIAL PHASE-SEPARATING GLASS AND GLASS CERAMIC ARTICLES AND LAMINATES," which mentions a copper containing laminate having a degradable phase, which phase liberates cooper ion, and a non-degradable phase, but does not claim priority thereto.

The entire disclosure of each publication or patent document mentioned herein is incorporated by reference.

BACKGROUND

The disclosure relates to bioactive glass compositions, and to methods of making and using the compositions.

SUMMARY

In embodiments, the disclosure provides:

a bioactive aluminoborate glass composition;

a group of aluminoborate glass compositions that individually, or in combination, have biocompatibility;

a group of aluminoborate glass compositions that individually, or in combination, promote angiogenesis;

aluminoborate glass compositions that can comprise, for example, a source of 30 to 60 mole % $B_2O_3$, 1 to 30 mole % $Al_2O_3$, 1 to 5 mole % $P_2O_5$, 3 to 30 mole % $Na_2O$, and 10 to 30 mole % CaO, based on a 100 mol % total of the composition;

aluminoborate glass compositions that can further comprise, for example, a source of 0.1 to 15 mole % $K_2O$, 0.1 to 15 mole % MgO, or a combination thereof, based on a 100 mol % total of the composition;

an article including at least one of the disclosed aluminoborate glass compositions, such as a dental or spinal prosthesis; and methods of making and methods of using the disclosed compositions.

BRIEF DESCRIPTION OF THE DRAWINGS

In embodiments of the disclosure.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed method of making and using provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"Glass," "glasses," or like terms can refer to a glass or a glass-ceramic.

"Glass article," or like terms can refer to any object made wholly or partly of glass or a glass-ceramic.

"Biocompatible," "biocompatibility," or like terms refer to the property or state of a substance that can coexist with living tissue, cells, or a living system ("bio-"), and for example, not being toxic or injurious, and not causing immunological rejection ("-compatible").

"Angiogenesis", "angiogenic", or like terms refers to the formation and differentiation of blood vessels, for example, in healthy tissue, cells, or organs, or diseased tissue, cells, or organs.

"Substantially free", "substantially free of", or like terms refers to the indicated species (e.g., $SiO_2$, SrO, or mixtures thereof; $Al_2O_3$) being entirely absent, or present in no more than incidental or trace amounts, for example, less than 10 to 100 ppm.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, times, and like aspects, and ranges thereof, are for illustration only; they do not exclude other defined values or other values within defined ranges. The composition and methods of the disclosure can include any value or any combination of the values, specific values, more specific values, and preferred values described herein, including explicit or implicit intermediate values and ranges.

Bioactive glasses have a widely recognized ability to foster the growth of bone cells, and to bond strongly with hard and soft tissues. Bioactive glasses are also reported to release ions that activate expression of osteogenic genes, and to stimulate angiogenesis (see Fu, Q, et al., Bioactive glass scaffolds for bone tissue engineering: state of the art and future perspectives, *Mater Sci Eng C*, 2011, 31: 1245-1256). More recently, there has been growing interest in bioactive borate glasses due to their novel properties such as fast degradation and conversion to hydroxyapatite-like materials, supporting angiogenesis, the regeneration of soft tissue, wound healing, and antimicrobial activity (see Rahaman, M. N., et al., Bioactive glass in tissue engineering, *Acta Biomater*, 2011, 7: 2355-2373). However, the fast release of boron into solution often results in decreased cell viability, especially for in vitro cell cultures. This can be solved by either modifying the glass composition to include some silica or culturing cells in a dynamic environment (see Rahaman, supra.).

The addition of $Al_2O_3$ to bioactive silicate glasses is generally avoided because $Al_2O_3$ inhibits the in vitro and in vivo formation of an appatite-layer on glass surface. The concentration of $Al_2O_3$ is controlled to be less than 3 wt % in silicate-based bioactive glasses (see Hench, L. L., Bioceramics, *J Am Ceram Soc*, 1998, 81: 1705-1728.). However, the impact of $Al_2O_3$ on the bioactivity of borate-based glasses remains unclear.

Peddi, L., et al., *J. Mater. Sci.: Mater. Med.*, 2008, vol. 19, No. 9, p. 3145, mentions bioactive borate glass coatings for titanium alloys.

US20090208428 mentions bioactive glass comprising Sr and $SiO_2$, wherein the Sr is provided as SrO and the mole equivalent percentage of SrO is 0.2% to 45%, and the bioactive glass is aluminum-free.

WO 2012137158, entitled "Bioactive glass compositions, their applications and respective preparation methods" mentions the development of bioactive glasses and glass-ceramics compositions that are able to promote a fast deposition layer of carbonated hydroxyapatite upon immersion in simulated body fluid (SBF) for time periods as short as one hour. Such compositions might include fluorides, and a variety of oxides (or their precursor compounds), such as $Na_2O$—$Ag_2O$—SrO—CaO—MgO—ZnO—$P_2O_5$—$SiO_2$—$Bi_2O_3$—$B_2O_3$—$CaF_2$, and prepared by the melt route or by the sol-gel process, with the specific compositions and the preparation route selected according to the intended functionalities, which can present controlled biodegradation rates and bactericidal activity.

In embodiments, the disclosure provides bioactive glass compositions having a higher $Al_2O_3$ content compared to prior compositions and the compositions are substantially free of $SiO_2$.

In embodiments, the disclosure provides an aluminoborate glass composition that is biocompatible. Boron release from these compositions immersed in an aqueous solution is substantially reduced compared to known compositions. The reduced borate release provides improved cell viability.

In embodiments, the disclosure provides a group of bioactive aluminoborate glass compositions. The glass compositions can comprise, consist of, or consist essentially of, a source of, for example, 30 to 60 mole % $B_2O_3$, 1 to 30 mole % $Al_2O_3$, 1 to 5 mole % $P_2O_5$, 3 to 30 mole % $Na_2O$, and 10 to 30 mole % CaO, based on a 100 mol % total of the composition.

In embodiments, the disclosed aluminoborate glass compositions can optionally further include, for example, 0.1 to 15 mole % $K_2O$, 0.1 to 15 mole % MgO, or a combination thereof, based on a 100 mol % total of the composition.

The inclusion of $Al_2O_3$ in the disclosed borate-based glass compositions causes a reduction in the amount of boron released into solution by, for example, an order of magnitude compared to the corresponding $Al_2O_3$-free borate-based glass compositions.

In embodiments, the disclosure provides one or more bioactive aluminoborate glass compositions that are biocompatible.

In embodiments, the disclosure provides methods of making and using the disclosed compositions.

In embodiments, the disclosure provides an aluminoborate glass composition, comprising, for example:
30 to 60 mol % $B_2O_3$,
1 to 30 mol % $Al_2O_3$,
1 to 5 mol % $P_2O_5$,
3 to 30 mol % $Na_2O$, and
10 to 30 mol % CaO, based on a 100 mol % total of the composition.

In embodiments, the above disclosed aluminoborate glass composition can further include or comprise, for example, at least one of: 0.1 to 15 mol % $K_2O$, 0.1 to 15 mol % MgO, or a combination thereof.

In embodiments, the disclosure provides a more preferred composition that can be, for example:
50 to 60 mol % $B_2O_3$,
2 to 20 mol % $Al_2O_3$, 1 to 3 mol % $P_2O_5$,
4 to 10 mol % $Na_2O$,
6 to 10 mol % $K_2O$,
6 to 10 mol % MgO, and
20 to 30 mol % CaO, based on a 100 mol % total of the composition.

In embodiments, the disclosure provides an even more preferred composition that can include, for example:
50 to 60 mol % $B_2O_3$,
2 to 10 mol % $Al_2O_3$,
1 to 3 mol % $P_2O_5$,
4 to 10 mol % $Na_2O$,
6 to 10 mol % $K_2O$,
6 to 10 mol % MgO, and
20 to 30 mol % CaO, based on a 100 mol % total of the composition.

In embodiments, the disclosed aluminoborate glass composition can include an $Al_2O_3$ content of, for example, from 10 to 15 mol % based on a 100 mol % total of the composition.

In embodiments, the disclosed aluminoborate glass composition can include an $Al_2O_3$ content of, for example, from 2 to 10 mol %.

In embodiments, the disclosed aluminoborate glass composition is substantially free of at least one of $SiO_2$, SrO, $Li_2O$, $Rb_2O$, $Cs_2O$, or mixtures thereof.

In embodiments, the disclosed aluminoborate glass composition is substantially free of SrO.

In embodiments, the disclosed aluminoborate glass composition is substantially free of $SiO_2$.

In embodiments, the disclosure provides a bioactive composition, comprising, for example:
at least one of the disclosed aluminoborate glass compositions or a mixture thereof; and
at least one live cell line, i.e., a bioactive composition including the glass composition and at least one cell or cells, such as an osteoblast cell, that are capable of synthesizing bone tissue.

In embodiments, the at least one live cell or cell line can be selected, for example, from the group consisting of osteoblasts, keratinocytes, human umbilical vein endothelial cells (HUVEC), and like cells or tissue, or combinations thereof.

In embodiments, the disclosure provides a method of limiting the amount of boron released, for example, as measured by a borate ion or like boron species, using any boron measurement method, into an aqueous solution from a aluminoborate-containing glass composition, comprising, for example:
contacting the aluminoborate-containing glass composition with an aqueous solution; wherein the aluminoborate-containing glass composition comprises sources of
30 to 60 mol % $B_2O_3$,
1 to 30 mol % $Al_2O_3$,
1 to 5 mol % $P_2O_5$,
3 to 30 mol % $Na_2O$, and
10 to 30 mol % CaO, based on a 100 mol % total of the composition.

In embodiments, the aluminoborate-containing glass composition can be prepared by, for example, melting a batch mixture of a borate-containing glass precursor and an $Al_2O_3$ source to form an aluminoborate-containing glass composition.

In embodiments, the batch mixture can comprise, for example, sources of
30 to 60 mol % $B_2O_3$,
1 to 30 mol % $Al_2O_3$,
1 to 5 mol % $P_2O_5$,
3 to 30 mol % $Na_2O$, and
10 to 30 mol % CaO, based on a 100 mol % total of the composition.

In embodiments, the method can further comprise, for example:
contacting, for example, immersing or covering the aluminoborate-containing glass composition with an aqueous solution; and
measuring the boron concentration in the aqueous solution over time.

In embodiments, the amount of $Al_2O_3$ in the batch mixture can be, for example, from 2 to 20 mol %.

In embodiments, the amount of boron released into the aqueous solution from the aluminoborate-containing glass composition can be reduced, for example, from 900 ppm to 50 ppm over a period of from 12 hrs to 10 days compared to an identical composition but that is free of the added $Al_2O_3$. In an exemplary boron release reduction or inhibition experiment, the boron release was reduced or inhibited from over 800 ppm to 100 ppm at 24 hr, from 1500 ppm to 150 ppm at 4 days, and from 1650 ppm to 185 ppm at 7 days, with respect to an $Al_2O_3$ free control composition.

In embodiments, the rate or kinetics of boron released into the aqueous solution from the aluminoborate-containing glass composition can be controlled by using an appropriate amount of $Al_2O_3$ or like sources of alumina. The optimal boron releasing rate or inhibition rate can depend on and be experimentally determined for a targeted application. For instance, for in vitro cell culture it is preferred to have a slow boron release rate that can be achieved by increasing the amount of $Al_2O_3$ in the glass composition. However, for in vivo applications such as the treatment of acid sensitive teeth or temperature sensitive teeth it is preferred to have a fast boron release rate by decreasing amount of $Al_2O_3$ in the glass composition, such that boron is quickly released, followed by hydroxyapatite build up or coating formation on the tooth surface or cavity.

Figure 1A:
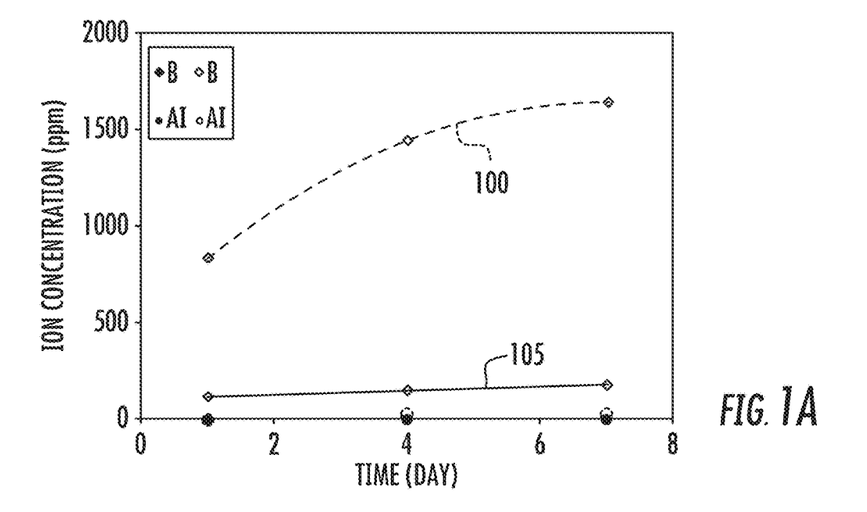
FIGS. 1A and 1B show the time dependent ion release (1A; borate and alumina ions) (1B; $Ca^{2+}$ ions) determined by inductively coupled plasma mass spectrometry (ICP) from glass powders of the comparative composition 1 (100) ($Al_2O_3$-free) and exemplary composition 4 (105) after immersion in simulated body fluid (SBF).
Figure 1B:
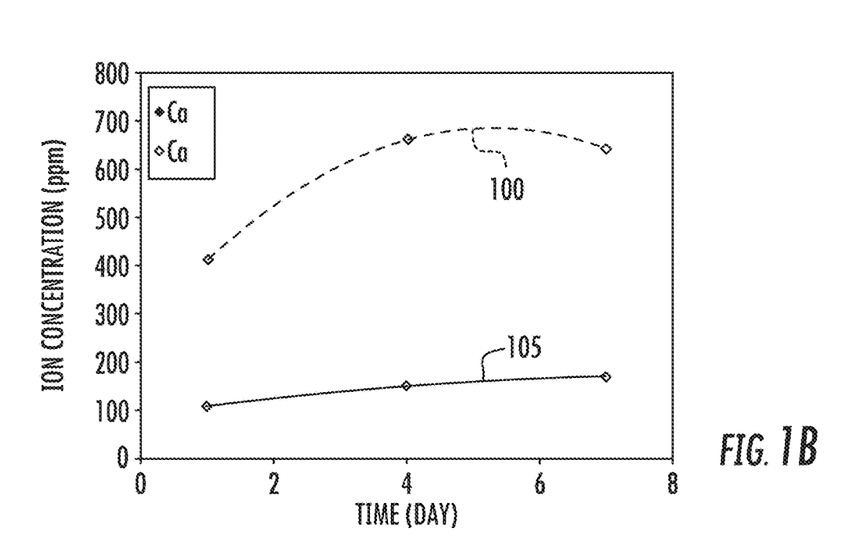

In embodiments, the amount of boron released into the aqueous solution from the disclosed aluminoborate-containing glass composition 3 (105) can be, for example, from 117 ppm to 185 ppm over a time period of from 0.5 to 10 days compared to an identical composition free of the added $Al_2O_3$. The comparative composition 1 (C-1) (100) had a released boron concentration of from 500 ppm to 1800 ppm, such as 841 to 1650 ppm over a time period of from 1 to 7 days (see FIGS. 1A and 1B). In embodiments, the aqueous solution can be, for example, a simulated body fluid (SBF) at a temperature of from 35 to 40° C., or a cell culture medium.

In embodiments, the disclosure provides a method of cell proliferation comprising:
contacting the disclosed aluminoborate glass compositions with a suitable liquid medium to create a bioactive composition.

In embodiments, the method of cell proliferation can further comprise or include contacting the bioactive composition, for example, with at least one cell, a cell line, a mixture of cells, or a mixture cell lines.

In embodiments, the disclosure provides a method of proliferating cells on a substrate comprising:
contacting a substrate comprised of at least one of the disclosed aluminoborate glass compositions with a suitable liquid medium in the presence of at least one cell.

In embodiments, the contacting can produce a proliferation of the at least one cell on the surface of the substrate by, for example, from 0.1 to 10 fold. In an exemplary demonstration, from day 4 to day 7, the cell number increased by an order of magnitude on composition 3 compared to the comparative composition 1 where the cell proliferation number remained zero.

In embodiments, the contacting can produce a proliferation of the at least one cell, for example, in the suitable liquid medium, on the substrate, or a combination thereof.

In embodiments, the suitable liquid medium can include, for example, a simulated body fluid composition.

In embodiments, the at least one cell can be or include, for example, a bone cell.

In embodiments, the contacting in the method of proliferating can produce, for example, an apatite or an hydroxyapatite (HA) compound on the surface of the substrate, such as an experimental glass disc, after SBF immersion.

In embodiments, the hydroxyapatite (HA) compound produced on the surface of the substrate can stimulate in vivo or in vivo bonding of the substrate to existing bone tissue.

In embodiments, the suitable liquid medium can include, for example, a simulated body fluid (SBF) composition (see for example, T. Kokubo, et al., "How useful is SBF in predicting in vivo bone bioactivity?," *Biomaterials*, 27[15] 2907-15 (2006), especially Appendix A. Recipe for preparing simulated body fluid (SBF) and procedure of apatite-forming ability test.).

In embodiments, the disclosed bioactive compositions can form in-situ a biologically active apatite layer (i.e., the mineral phase of bone and teeth) that bonds to bone and teeth, and can even bond to soft tissue. The applications of bioactive compositions can include, for example, monolithic articles, composites, fibers, powers, discs, beads, films, coatings, or like forms, for use in, for example, repair of load-bearing bones, dental regeneration, treatment of dental hypersensitivity, artificial vertebrae, spinous spacers, intervertebral spacers, iliac spacers, granular fillers, scaffolds, middle-ear implant and in other types of small-bone replacement, wound healing, and like applications. The disclosed bioactive compositions are biocompatible with, for example, osteoblasts, keratinocytes, human umbilical vein endothelial cells (HUVEC), and like biocompatibilities.

In embodiments, the disclosure provides an article comprising:
at least one of the disclosed aluminoborate glass compositions, wherein the article is at least one of: biocompatible; angiogenic, or a combination thereof.

The disclosed compositions are "biocompatible", which indicates that it can support cell growth and proliferation without being toxic or reactive with the cells, and "biologically active" (i.e., bioactive), which indicates that the disclosed compositions can be converted to an hydroxyapatite (HA)-like material that can support in vivo bone bonding.

In embodiments, the disclosed compositions and methods thereof are advantaged in several aspects, including for example:

Applicant has unexpectedly discovered that the addition of $Al_2O_3$ to the borate glass composition improves the biocompatibility of the resulting bioactive glass compositions;

the disclosed $Al_2O_3$ borate glass compositions have a substantially decreased boron release rate when the composition is immersed in solution compared to comparable $Al_2O_3$ free compositions; and the disclosed $Al_2O_3$ borate glass compositions have a glass dissolution or degradation rate in a solution that can be substantially decreased compared to an equivalent but $Al_2O_3$-free borate glass composition.

In embodiments, the disclosure provides aluminoborate glass compositions having excellent biocompatibility. The disclosed glass compositions comprise a source of, for example, 30 to 60 mole % $B_2O_3$, 1 to 30 mole % $Al_2O_3$, 1 to 5 mole % $P_2O_5$, 3 to 30 mole % $Na_2O$, and 10 to 30 mole % CaO, based on a 100 mol % total of the composition. A more preferred compositional range can be, for example, 50 to 60 mol % $B_2O_3$, 2 to 20 mol % $Al_2O_3$, 1 to 3 mol % $P_2O_5$, 4 to 10 mol % $Na_2O$, 6 to 10 mol % $K_2O$, 6 to 10 mol % MgO, and 20 to 30 mol % CaO, based on a 100 mol % total of the composition. Example compositions are listed in Table 1.

Table 1 shows examples of disclosed compositions. Anneal and strain points were determined by beam bending viscometry. The coefficient of thermal expansion (CTE) is the average value between ambient or room temperature (e.g., 25° C.) and 300° C.

TABLE 1

Exemplary disclosed compositions and properties.

| Oxides (mol %) | Comp 1[1.] | 2 | 3 | 4 | 5 | 6 | Comp 7[1.] | 8 | 9 |
|---|---|---|---|---|---|---|---|---|---|
| $B_2O_3$ | 54.6 | 54.6 | 54.6 | 42.6 | 38.6 | 34.6 | 46.1 | 46.1 | 46.1 |
| $Al_2O_3$ | 0 | 4 | 8 | 12 | 16 | 20 | 0 | 4 | 8 |
| $P_2O_5$ | 1.7 | 1.7 | 1.7 | 1.7 | 1.7 | 1.7 | 2.6 | 2.6 | 2.6 |
| $Na_2O$ | 6 | 6 | 6 | 6 | 6 | 6 | 24.4 | 24.4 | 24.4 |
| $K_2O$ | 7.9 | 7.9 | 7.9 | 7.9 | 7.9 | 7.9 | 0 | 0 | 0 |
| MgO | 7.7 | 7.7 | 7.7 | 7.7 | 7.7 | 7.7 | 0 | 0 | 0 |
| CaO | 22.1 | 22.1 | 22.1 | 22.1 | 22.1 | 22.1 | 26.9 | 26.9 | 26.9 |
| Properties | | | | | | | | | |
| CTE ($\times 10^{-7}$/° C.) | 102 | 103 | 100 | — | — | — | — | 129 | 123 |
| Strain pt (° C.) | 463 | 462 | 457 | — | — | — | — | 422 | 420 |
| Anneal pt (° C.) | 494 | 493 | 488 | — | — | — | — | 449 | 449 |

[1.]Comp = Comparative Example (C-#)

Comparative 7 is a prior art composition (see Huang, et al., "Kinetics and mechanisms of the conversion of silicate (45S5), borate and borosilicate glasses to hydroxyapatite in dilute phosphate solutions," *J Mater Sci Mater Med* 2006, 17: 583-596).

The disclosed glass compositions can typically be prepared by melting the source components at, for example, a temperature below 1300° C., and in certain embodiments below 1200° C., making it possible to melt in a relatively small commercial glass melting tank.

In embodiments, the addition of $Al_2O_3$ to borate glass compositions can lower or inhibit the release of boron ion to a solution by almost an order of magnitude. Analogously, the addition of $Al_2O_3$ to borate glass compositions caused the release of Ca ion to be decreased but only by about half (FIG. 1). The decreased amount of boron in a solution is significant for cell viability since a high amount of boron released into the solution often results in cell toxicity, while the release of Ca ion is reported to improve the bioactivity of glasses since Ca ion is critical to cell attachment (see Hench, L. L., et al., Third-generation biomedical materials. *Science*, 2002, 295:1014-1017). Furthermore, the rate of weight loss of the disclosed $Al_2O_3$-containing glasses is much slower or lower than the $Al_2O_3$-free borate glasses (FIG. 2), suggesting that a controllable degradation can be achieved through compositional modification, in particular, by controlling or adjusting the amount of $Al_2O_3$.

Figure 2:
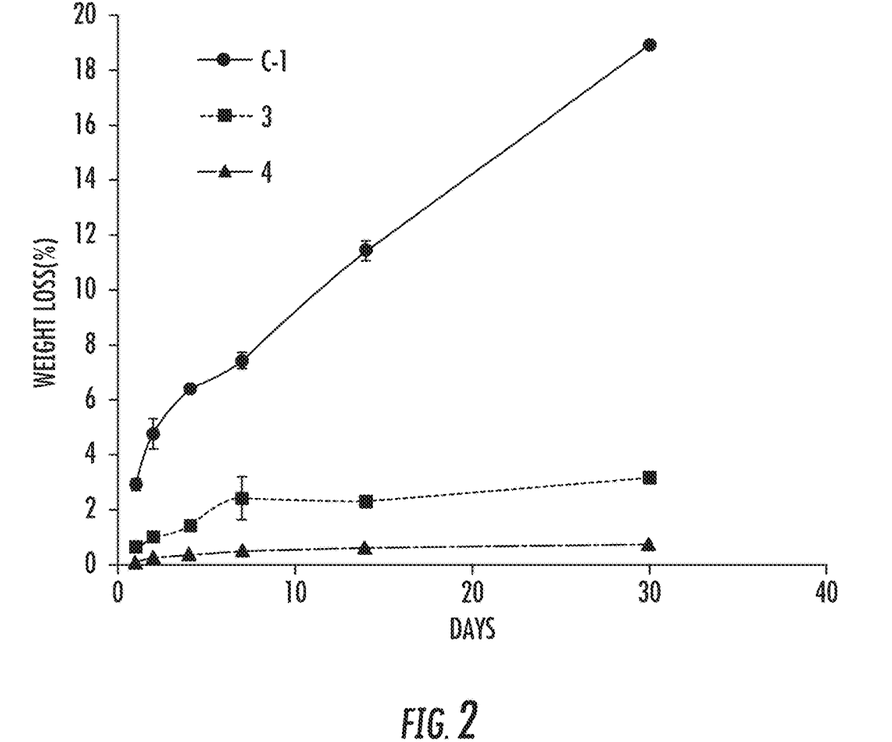
FIG. 2 shows weight loss results (wt %) over time for exemplary disclosed compositions 3 and 4, and a comparative composition 1 (C-1) when immersed in simulated body fluid (SBF) solution at 37° C. for 30 days.

FIG. 2 shows weight loss results (weight %) over time for exemplary disclosed compositions 3 and 4, and a comparative composition 1 when immersed in simulated body fluid (SBF) solution at 37° C. for 30 days. After 1 day of SBF immersion, comparative composition 1 (C-1) and exemplary compositions 3 ("3") and 4 ("4") had a respective weight losses of 3 wt %, 0.7%, and 0.2%; after 1 week of SBF immersion, comparative composition 1 (C-1) and exemplary compositions 3 ("3") and 4 ("4") had a respective weight losses of 7.5 wt %, 2.4%, and 0.5%; and after 1 month of SBF immersion, comparative composition 1 (C-1) and exemplary composition 3 ("3") and 4 ("4") had a respective weight losses of 18.9 wt %, 3.2%, and 0.8%. The FIG. 2 results demonstrate that the inclusion of alumina in the comparative alumina-free composition resulted in the disclosed alumina containing compositions having reduced weight loss when immersed in an SBF solution. The disclosed alumina containing compositions had better durability with respect to dissolution or solution degradation than the corresponding alumina-free borate glass compositions.

The slower or lower degradation rate in the disclosed $Al_2O_3$-containing glasses was also confirmed by the surface morphology observed using SEM (FIG. 3). A rough surface composed of fine crystals was observed in the $Al_2O_3$-free borate glass but not in the disclosed $Al_2O_3$-containing glass borate glass.

Figure 3A:
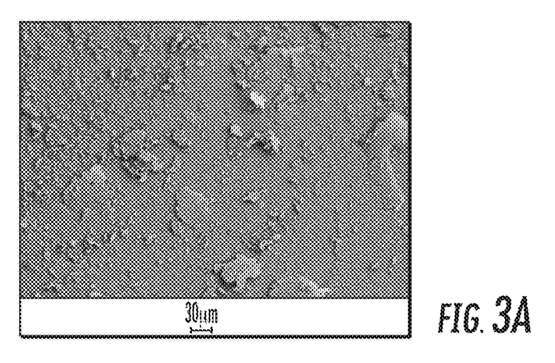
FIGS. 3A to 3C show SEM images demonstrating the change in surface morphology of comparative (3A) and inventive compositions (3B and 3C) after immersion in SBF for 7 days.
Figure 3B:
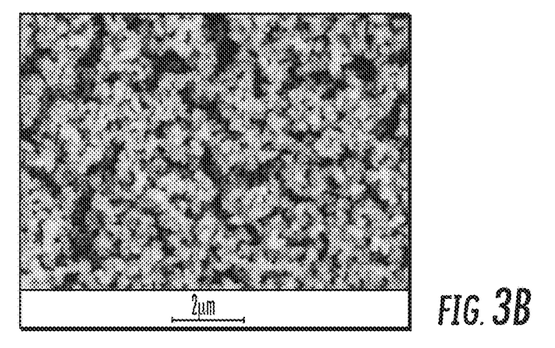
Figure 3C:
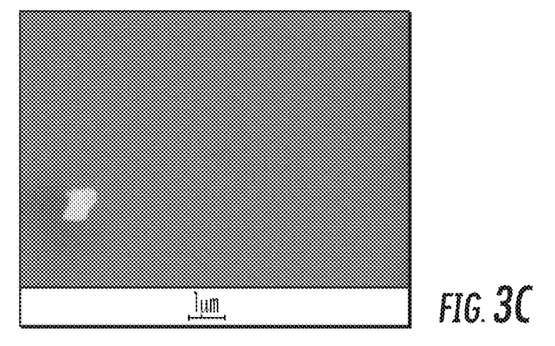

FIGS. 3A to 3C show SEM images demonstrating the change in surface morphology of comparative composition 1 (3A)(0 mol % $Al_2O_3$, at a 30 micron scale); inventive composition 2 (3B)(4 mol % $Al_2O_3$ at a 2 micron scale), and inventive composition 3 (3C)(8 mol % $Al_2O_3$ at a 1 micron scale) after immersion in SBF for 7 days.

Figure 4A:
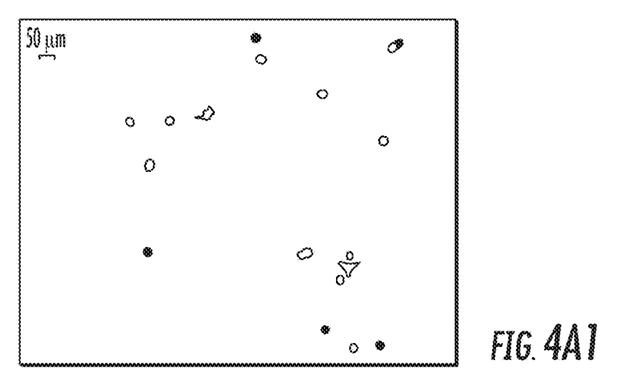
FIGS. 4A and 4B show optical images of cell morphology from live/dead cells assay cultured on a comparative (FIGS. 4A: 4A1, 4A2, and 4A3) and an inventive (FIGS. 4B: 4B1, 4B2, and 4B3) glass disc.
Figure 4A:
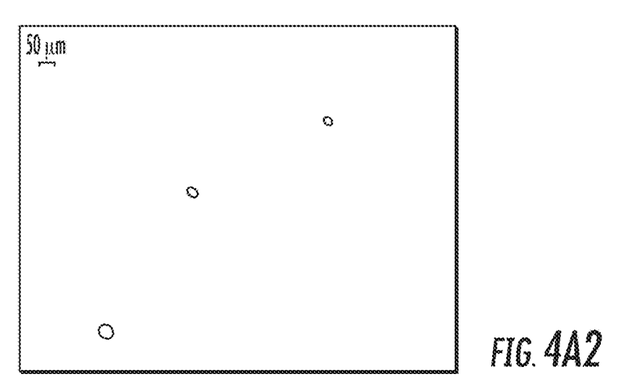
Figure 4A:
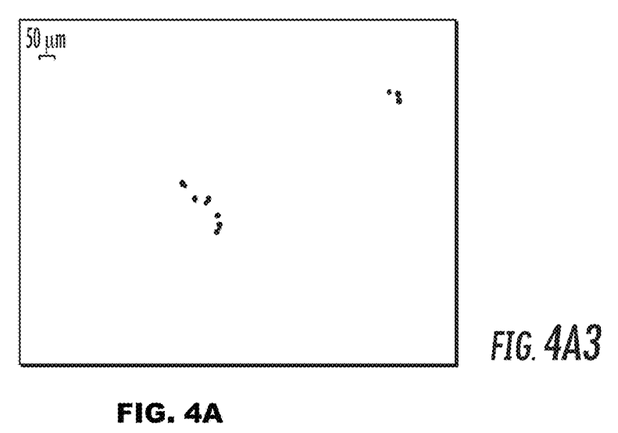
Figure 4B:
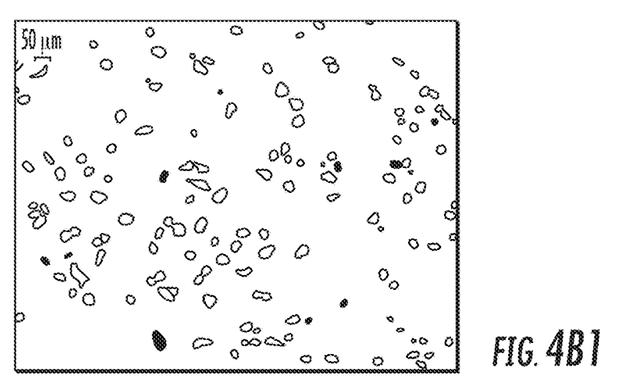
Figure 4B:
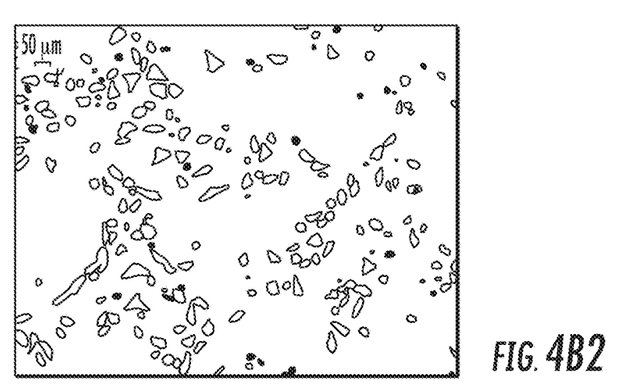
Figure 4B:
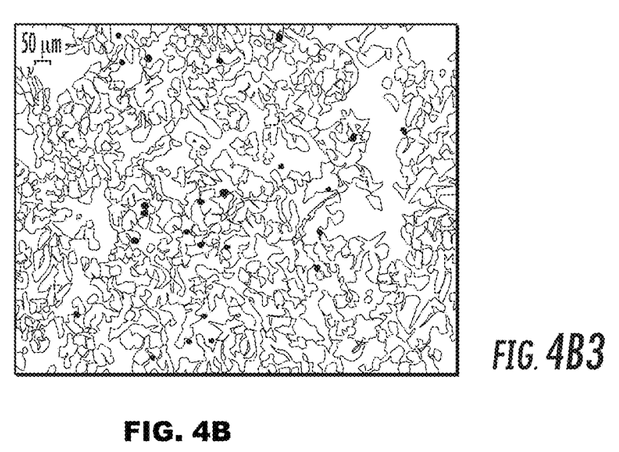

FIGS. 4A and 4B show optical images of cell morphology from live/dead cells assay cultured on a glass disc. Cell culture was accomplished on a bioactive glass disc (12.5 mm diameter×2.0 mm thick) made from comparative composition 1 (4A1 at Day 1; 4A2 at Day 4; and 4A3 at Day 7); and composition 3 (4B1 at Day 1; 4B2 at Day 4; and 4B3 at Day 7) in a 24-well culture plate. The unshaded and outlined open forms, such as ovals or circles represent the viable live cells and the shaded forms, such as black spots, dots, or black circles represent dead cells. The disclosed composition 3 exhibits significant live cells and minimal dead cells after Day 7.

Figure 5:
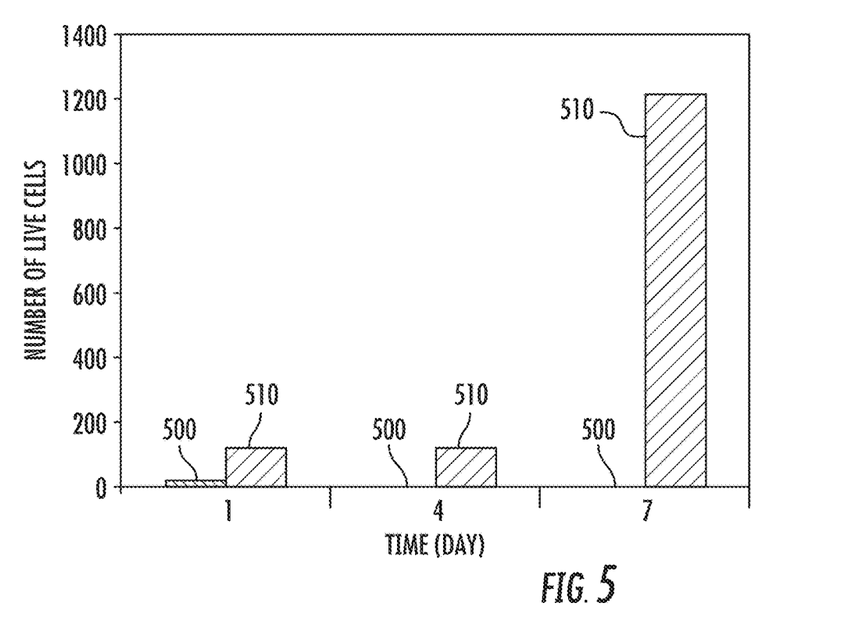
FIG. 5 shows a bar chart of viable cell counts as a function of culture time in comparative composition 1 (500) and inventive composition 3 (510).

FIG. 5 shows a bar chart of viable cell counts as a function of culture time in comparative composition 1 (500) and inventive composition 3 (510). Cell culture was accomplished on a bioactive glass disc (12.5 mm diameter×2.0 mm thick) in a 24-well culture plate.

In embodiments, improved biocompatibility was demonstrated in the disclosed aluminoborate glasses. A substantially higher number of viable cells were seen in an inventive aluminoborate glass than in a comparative $Al_2O_3$-free borate glass (FIG. 4). There were no viable cells on the comparative $Al_2O_3$-free borate glass (500) after 4 days. Furthermore, the cell counts continued to increase in a disclosed aluminoborate composition (510) through Day 7 (FIG. 5). Although not limited by theory, the excellent biocompatibility demonstrated for the disclosed aluminoborate glass compositions is believed to be attributable to the alumina source, which lowers or slows boron ion release rate as observed in FIG. 1.

In embodiments, the disclosed glasses can be processed by various suitable techniques into, for example, powder, short fibers, beads, sheets, 3-D scaffolds, and like form factors. Glass powder can be generally prepared by, for example, jet milling or ball milling of glass frits. Short fibers can be made by, for example, melt spinning or electric spinning. Beads can be produced by flowing glass particles through a vertical furnace. Sheets can be made using, for example, thin rolling, float, or fusion-draw processes. Scaffolds can be made using, for example, rapid prototyping, polymer foam replication, particle sintering, and like methods. Glasses of desired form factors can be used in methods, for example, to support cell growth, soft and hard tissue regeneration, stimulation of gene expression or angiogenesis, and like applications.

In embodiments, the disclosed compositions can influence the biocompatibility and degradation of the compositions. In embodiments, the disclosed compositions, the $B_2O_3$ serves as the primary glass-forming oxide. Borate glass is much less durable than silicate glass, making it attractive for fast degradation. However, the toxicity caused by the degradation and the control of the degradation rate remain a big challenge.

In embodiments, the $P_2O_5$ can also serve as a network former. Furthermore, the liberation of phosphate ions to the surface of bioactive glasses can contribute to the formation of apatite. The provision of phosphate ions by the bioglass can increase the rate of apatite formation and the binding capacity of bone tissue. In addition, $P_2O_5$ can increase the melt viscosity of the glass, which in turn expands the range of operating temperatures, and is advantageous in the formation and manufacture of the disclosed glass.

In embodiments, the $Al_2O_3$ can also serve as a glass former in the disclosed glasses. The $Al_2O_3$ generally increases the viscosity of the melt, and an increase in $Al_2O_3$ relative to the alkalis or alkaline earths generally results in improved durability. The structural role of the aluminum ions depends on the glass composition. However, $Al_2O_3$ is generally not present in silicate-based bioactive glasses since it substantially decreases their bioactivity.

In embodiments, the alkali oxides ($Na_2O$, and $K_2O$) can serve as aids in achieving a low melting temperature and low liquidus temperatures. Additionally, the addition of alkali oxides has been reported to improve bioactivity (see Hench, L. L., *Bioceramics*, supra.).

In embodiments, the divalent cation oxides (such as alkaline earth oxides; MgO and CaO) can also be used to improve the melting behavior and the bioactivity of the glass. Particularly, CaO has been found to react with $P_2O_5$ to form apatite when immersed in a simulated body fluid (SBF) or in vivo. The release of $Ca^{2+}$ ions from the surface of the glass contributes to the formation of a layer rich in calcium phosphate.

EXAMPLES

The following Examples demonstrate making, use, and analysis of the disclosed compositions and methods in accordance with the above general procedures.

Example 1

Preparation of Example Compositions 2 to 6

Example Compositions 2 to 6 listed in Table 1, and their respective source batch materials in the indicated amounts, including boric acid, alumina, sodium carbonate, potassium carbonate, limestone, magnesia and calcium phosphate, were individually combined and melted in an electric furnace. Prior to melting, the batch source materials were vigorously mixed in a plastic jar using a Turbula® mixer. Then they were transferred to a platinum crucible with an internal volume of approximately 650 cc. The crucible was then loaded into an annealing furnace to calcine the batch at 250° C. for 24 hr. The calcined batches were the melted at 1200° C. for 6 hr and then the glass melt was poured on a steel plate, and annealed at 500° C.

Example 2

Comparative Example Compositions 1 and 7

Example 1 was repeated with the exception that the source ingredients exclude $Al_2O_3$, and included $K_2O$ and MgO, to respectively, produce Comparative Example 1 and Comparative Example 7 samples, specified in Table 1.

Example 3

Preparation of Example Compositions 8 to 9

Example 1 was repeated with the exception that the source ingredients excluded $K_2O$ and MgO, to produce samples of Examples 8 to 9.

Example 4

In Vitro Immersion in SBF

The influence of glass composition on the glass degradation was studied by measuring the ion release from and weight loss of example glasses. Glass discs (12.5 mm in diameter×2 mm in thickness) were prepared by core drilling discs from a melted glass patty of an inventive or comparative glass composition and then polishing the discs using a $CeO_2$ paste. The glass disc was immersed in a simulated body fluid (SBF) kept in a polyethylene bottle at 37° C., and the glass to SBF weight ratio was maintained at 1:100. After soaking for one, four, and seven days, a small amount of SBF (5 mL) was removed from the bottle and the ions in the solution were measured using inductively coupled plasma (ICP). The mass of the glass discs were weighed before and after SBF immersion to determine the weight loss attributable to contact with the SBF. The surface morphology of the SBF-soaked example glass discs was examined by scanning electron microscopy (SEM). Discs were coated with carbon prior to the examination to reduce surface charging (see T. Kokubo, supra., for the recipe for SBF).

Example 5

Cell Culture on Glass Discs

Example glass discs (in duplicate), having a diameter of 12.5 mm and a thickness of 2.0 mm, were individually placed into wells of tissue culture treated microplates. For an individual microplate, two wells without any glass discs were included as a control. Saos-2 cells (from ATCC), human osteoblast-like cells, were seeded onto each example glass disc and controlled to a density of 20,000/2 mL/well. The Saos-2 cell culture medium is composed of McCoy's 5a Medium Modified containing 15% fetal bovine serum. Cells were cultured at 37° C. for 1 day, 4 days, and 7 days before live/dead staining using Calcein AM and Ethidium homodimer-1 fluorescent dyes. The medium was changed at day 1 and then every other day subsequently. The images were obtained with a fluorescent microscope. The cell number was counted using ImageJ software. Significantly better biocompatibility was observed in $Al_2O_3$-containing borate glasses (see FIG. 4).

Example 6

Inhibition of Hydroxyapatite Formation

A one week SBF soaking study using the above mentioned discs as test substrates showed that the inclusion of 4 mol % $Al_2O_3$ in the disclosed composition caused a relative reduction or inhibition in apatite formation on the surface of the substrate compared to a comparable composition having 0 mol % $Al_2O_3$. The inclusion of 8 mol % $Al_2O_3$ completely inhibited apatite formation on the surface of the substrate.

Example 7

Angiogenesis Activity

Each disclosed inventive composition was tested for angiogenesis ability. A 24 well tissue culture treated (TCT) microplate, human Umbilical Vein Endothelial Cells (HU-VEC-2), Matrigel®, and Calcein AM fluorescent dye were from Corning®, Inc. EBM™ Basal Medium and EGM™-2 SingleQuots™ Kit were from Lonza.

The procedure for angiogenesis evaluation follows. Example glass discs (in duplicate), having a diameter of 12.5 mm and a thickness of 2.0 mm, were individually placed into wells of tissue culture treated microplates. For an individual microplate, two controls were included: in two wells were placed gelatin-coated coverslips and in two wells there were no glass discs or gelatin-coated coverslips. The TCT microplates were kept on ice (0° C.), and 400 microliters of Matrigel® were added to each well. Then the TCT microplates were incubated at 37° C. for 30 to 60 mins before HUVEC-2 cells were seeded on the top of Matrigel® in each of the wells with the cell density of from about $1.2 \times 10^8/2$ mL/well. HUVEC-2 culture medium was composed of Lonza EBM™ Basal Medium containing 2% fetal bovine serum, ascorbic acid, hydrocortisone, human epidermal growth factor (hEGF), vascular endothelial growth factor (VEGF), insulin-like growth factor-1 (IGF-1), human fibroblast growth factor-beta (hFGF-β), and heparin. The angiogenesis assay microplates were incubated at 37° C. for 16 to 18 hrs in 5% $CO_2$ humid atmosphere. The images were taken using a fluorescent micro scope. The tube formation was measured by counting the loop number after labeling with Corning® Calcein AM fluorescent dye. The incorporation of Al$_2$O$_3$ into the disclosed borate-based glass compositions inhibited apatite information. The inclusion of 8 mol % Al$_2$O$_3$ into the disclosed borate-based glass compositions increased angiogenesis.

Figure 6A:
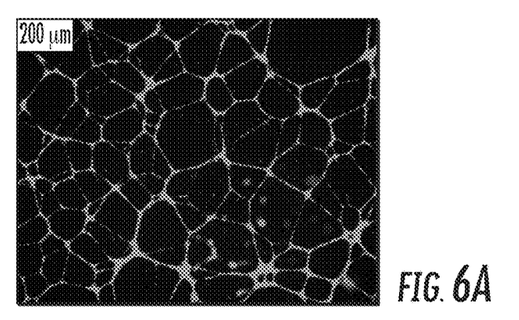
FIGS. 6A to 6D show angiogenesis results for a comparative composition and representative disclosed compositions.
Figure 6B:
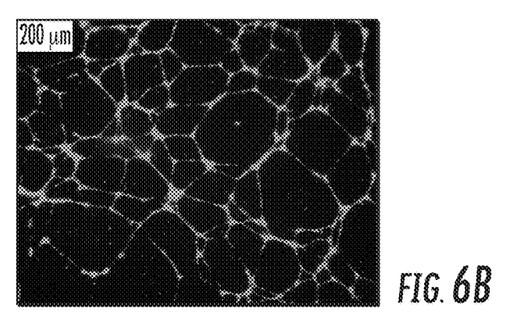
Figure 6C:
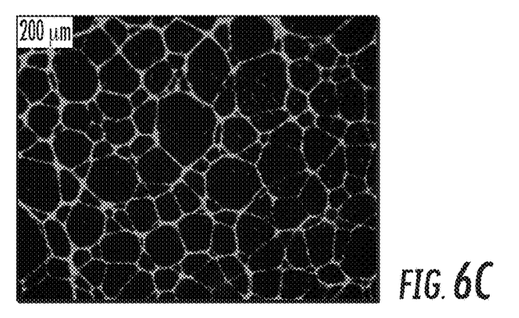
Figure 6D:
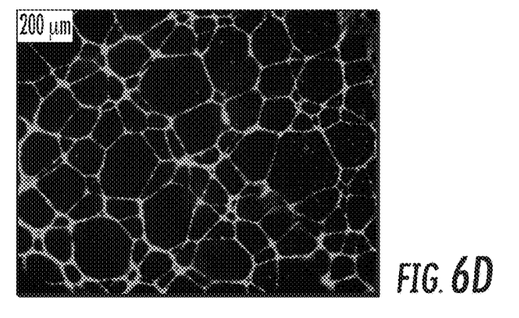

FIGS. 6A to 6D show the angiogenesis results for a comparative composition and disclosed compositions for Matrigels sitting on: a TCT plastic surface (FIG. 6A), and glass discs (12.5 mm diameter×2.0 mm thick) of comparative composition 1 (FIG. 6B), inventive composition 3 (FIG. 6C), and inventive composition 4 (FIG. 6D). Compared to the TCT plastic surface (89 tube loops), the comparative composition 1 (C-1)(Al free) had reduced angiogenesis (53 tube loops). The inventive compositions 3 and 4 had an increased angiogenesis (109 and 99 tube loops, respectively). Compared to the comparative composition 1, the inventive compositions 3 and 4, respectively, had a 2.1 and a 1.9 fold higher angiogenesis, indicating or suggesting that controlled ionic release can be a significant factor in an angiogenic response to bioactive glass compositions.

The disclosure has been described with reference to various specific embodiments and techniques. However, it should be understood that many variations and modifications are possible while remaining within the scope of the disclosure.

What is claimed is:

1. A bioactive composition, comprising:
   an aluminoborate glass composition, consisting of:
      30 to 60 mol % B$_2$O$_3$,
      8 to 30 mol % Al$_2$O$_3$,
      1 to 5 mol % P$_2$O$_5$,
      3 to 30 mol % Na$_2$O,
      10 to 30 mol % CaO, and
      balance of at least one alkali or alkaline earth metal oxide, based on a 100 mol % total of the composition; and
   at least one live cell.

2. The bioactive composition of claim 1, wherein the at least one alkali or alkaline earth metal oxide comprises: 0.1 to 15 mol % K$_2$O, 0.1 to 15 mol % MgO, or a combination thereof.

3. The bioactive composition of claim 1 wherein the Al$_2$O$_3$ content is from 10 to 15 mol %.

4. The bioactive composition of claim 1, wherein the at least one live cell is selected from the group consisting of an osteoblast, a keratinocyte, a human umbilical vein endothelial cell (HUVEC), or combinations thereof.

5. A method of controlling the rate of boron released into an aqueous solution from an aluminoborate-containing glass composition, comprising:
   contacting the aluminoborate-containing glass composition with an aqueous solution; wherein the aluminoborate-containing glass composition comprises sources of:
      30 to 60 mol % B$_2$O$_3$,
      8 to 30 mol % Al$_2$O$_3$,
      1 to 5 mol % P$_2$O$_5$,
      3 to 30 mol % Na$_2$O,
      10 to 30 mol % CaO, and
      balance of at least one alkali or alkaline earth metal oxide, based on a 100 mol % total of the composition,
   wherein the amount of Al$_2$O$_3$ controls the amount of boron released into the aqueous solution or the boron release kinetics of the composition.

6. The method of claim 5, wherein the at least one alkali or alkaline earth metal oxide comprises 6 to 10 mol % K$_2$O, 6 to 10 mol % MgO, or a combination thereof, in the aluminoborate-containing glass composition.

7. The method of claim 5 further comprising measuring the boron concentration in the aqueous solution over time.

8. The method of claim 5 wherein the amount of boron released into the aqueous solution from the aluminoborate-containing glass composition is reduced from 900 ppm to 50 ppm over a period of from 12 hrs to 10 days compared to an identical composition except that the identical composition is free of Al$_2$O$_3$.

9. The method of claim 6 wherein the amount of boron released into the aqueous solution from the aluminoborate-containing glass composition is from 10 ppm to 100 ppm over a time period of from 0.5 to 10 days compared to an identical composition except that the identical composition is free of Al$_2$O$_3$ and having a concentration of boron released of from 500 ppm to 1800 ppm over a time period of from 0.1 to 8 days.

10. The method of claim 5 wherein the aqueous solution is a simulated body fluid (SBF) at a temperature of from 35 to 40° C.

11. A method of proliferating cells on a substrate comprising:
   contacting a substrate comprised of the aluminoborate glass composition of claim 1 with a suitable liquid medium in the presence of at least one cell.

12. The method of claim 11 wherein the contacting produces a proliferation of the at least one cell on the surface of the substrate by from 0.1 to 10 fold, compared to the proliferation in an alumina free composition.

13. The method of claim 11 wherein the contacting produces a proliferation of the at least one cell in the suitable liquid medium, on the substrate, or both.

14. The method of claim 11 wherein the suitable liquid medium includes a simulated body fluid composition and the at least one cell is a bone cell.

15. The method of claim 14 wherein the contacting produces a hydroxyapatite (HA) compound on the surface of the substrate that stimulates in vitro or in vivo bonding to bone.

16. An article comprising:
   the aluminoborate glass composition of claim 1, wherein the article is at least one of biocompatible, angiogenic, or a combination thereof.

* * * * *

UNITED STATES PATENT AND TRADEMARK OFFICE
CERTIFICATE OF CORRECTION

PATENT NO. : 10,647,962 B2
APPLICATION NO. : 15/602819
DATED : May 12, 2020
INVENTOR(S) : Huayun Deng et al.

Page 1 of 2

It is certified that error appears in the above-identified patent and that said Letters Patent is hereby corrected as shown below:

On the Title Page

On page 2, in Column 2, Item (56), Other Publications, Line 20, delete "baed" and insert -- based --, therefor.

On page 2, in Column 2, Item (56), Other Publications, Line 21, delete "Sciemce:" and insert -- Science: --, therefor.

On page 3, in Column 1, Item (56), Other Publications, Line 59, delete "(2003." and insert -- (2003). --, therefor.

On page 3, in Column 1, Item (56), Other Publications, Line 61, delete "136145)." and insert -- (136145). --, therefor.

On page 3, in Column 1, Item (56), Other Publications, Line 63, delete "SiO2Na20." and insert -- SiO2Na2O. --, therefor.

On page 3, in Column 1, Item (56), Other Publications, Line 68, delete "Microplasitcs" and insert -- Microplastics --, therefor.

On page 3, in Column 2, Item (56), Other Publications, Line 9, delete "Manetization" and insert -- Magnetization --, therefor.

On page 3, in Column 2, Item (56), Other Publications, Line 41, delete "Propmotes" and insert -- Promotes --, therefor.

On page 3, in Column 2, Item (56), Other Publications, Line 50, delete "Additiona" and insert -- Additional --, therefor.

Signed and Sealed this
Eleventh Day of October, 2022

Katherine Kelly Vidal
*Director of the United States Patent and Trademark Office*

CERTIFICATE OF CORRECTION (continued)
U.S. Pat. No. 10,647,962 B2

On page 3, in Column 2, Item (56), Other Publications, Line 52, delete "Internaitonal;" and insert -- International; --, therefor.

On page 3, in Column 2, Item (56), Other Publications, Lines 56-57, delete "Si02--Na20--Fe203--Ca0--P205_B203" and insert -- SiO2--Na2O--Fe2O3--CaO--P2O5_B2O3 --, therefor.

On page 3, in Column 2, Item (56), Other Publications, Line 58, delete "(1999." and insert -- (1999). --, therefor.

On page 3, in Column 2, Item (56), Other Publications, Line 66, delete "(2007." and insert -- (2007). --, therefor.

On page 4, in Column 1, Item (56), Other Publications, Line 8, delete "stronium" and insert -- strontium --, therefor.

On page 4, in Column 1, Item (56), Other Publications, Line 19, delete "ArticleI D" and insert -- ArticleID --, therefor.

In the Specification

In Column 1, Line 13, delete "Applications" and insert -- Application --, therefor.